United States Patent
Sakai et al.

(10) Patent No.: US 6,946,430 B2
(45) Date of Patent: Sep. 20, 2005

(54) SURFACTANT COMPOSITION

(75) Inventors: Takaya Sakai, Wakayama (JP); Makoto Kubo, Wakayama (JP); Makio Tetsu, Wakayama (JP); Youhei Kaneko, Wakayama (JP)

(73) Assignee: Kao Corporation, Tokyo (JP)

( * ) Notice: Subject to any disclaimer, the term of this patent is extended or adjusted under 35 U.S.C. 154(b) by 117 days.

(21) Appl. No.: 10/105,415

(22) Filed: Mar. 26, 2002

(65) Prior Publication Data

US 2002/0187915 A1 Dec. 12, 2002

(30) Foreign Application Priority Data

Mar. 28, 2001 (JP) ........................................ 2001-092075

(51) Int. Cl.$^7$ .............................. C11D 1/02; C11D 1/83; C11D 3/36; C11D 3/32
(52) U.S. Cl. ....................... 510/126; 510/127; 510/130; 510/137; 510/138; 510/155; 510/156; 510/158; 510/159; 510/495; 510/502; 510/506; 510/467
(58) Field of Search ................................ 510/126, 127, 510/130, 137, 138, 155, 156, 158, 159, 495, 502, 506, 467

(56) References Cited

U.S. PATENT DOCUMENTS 6,407,054 B2 * 6/2002 Sakai et al. ................. 510/501
6,514,918 B1 * 2/2003 Librizzi ...................... 510/124

2002/0193266 A1 * 12/2002 Matsumoto et al. ........ 510/130

FOREIGN PATENT DOCUMENTS

JP 09159169 * 12/1998

* cited by examiner

*Primary Examiner*—Gregory R. Del Cotto
(74) *Attorney, Agent, or Firm*—Oblon, Spivak, McClelland, Maier & Neustadt, P.C.

(57) ABSTRACT

To provide a surfactant composition with an excellent foamability and thickening performance and further an excellent storage stability, it comprises the following components (a) and (b):

(a) at least one anionic surfactant selected from (1) sulfonate-type anionic surfactants having amide group or ester group, (2) carboxylate-type anionic surfactants and (3) phosphate-type anionic surfactants and (b) a compound expressed by the formula (I):

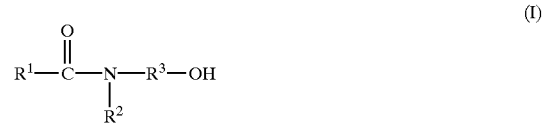

where $R^1CO—$ is an acyl group having 6 to 24 carbon atoms, $R^2$ is an alkyl group having 1 to 3 carbon atoms and $R^3$ is an alkylene group having 1 to 6 carbon atoms or an alkenylene group having 2 to 6 carbon atoms.

15 Claims, No Drawings

SURFACTANT COMPOSITION

TECHNICAL FIELD OF THE INVENTION

The present invention relates to a surfactant composition having an excellent foamability, thickening performance and water solubility and further an excellent storage stability.

PRIOR ARTS

Not only a high detergency but also an abundant foaming are requested to a detergent such as a shampoo, a rinse, a solid soap, a body shampoo, a detergent for kitchens, a detergent for clothing and a detergent for dwellings. One which has been widely used as the main base in many products is an anionic surfactant such as an alkyl benzenesulfonate (LAS), an alkyl sulfate salt (AS) and a polyoxyethylene alkyl sulfate salt (AES) However, although any thereof usually shows its excellent detergency and foaming, there is a problem therein that, when solids, a stain derived from silicone or the like is present, the detergency and foamability significantly lower.

Further, in the recent trend of seeking detergents small in load to the human body and the environment, anionic surfactants of the base are not limited to LAS, AS, or AES, but various surfactants have come to be used widely. Examples are diversified, including carbonates using alkyl phosphate or amino acid as the raw material, and sulfonates and carbonates using amide group, ester group, or other functional group to seek safety and biodegradable property. These surfactants used as the base generally tend to lower in detergency and formability as the diversity is emphasized.

In order to improve such a lowering in detergency and/or foamability, various co-surfactants besides the main base have been investigated. There have been first proposed a fatty acid diethanolamide which has been actually and widely used in the products and then proposed in recent years a fatty acid monoethanolamide (WO 98/0507, WO 97/44434, JP-A11-80785, etc.), a sugar amide-type nonionic surfactant(WO 94/12610), an acylsarcosinate (WO 96/06596), etc. However, although these detergent compositions are improved in detergency and foamability, they are not well satisfactory yet.

JP-A 2001-34310, being equivalent to WO 01/40421 published on Jun. 7, 2001 corresponding to EP-A 1149892, discloses an ethanol amide compound.

It is also important to suppress separation of a blend caused in storage or adjust the viscosity of the blend so adequately as to produce a proper comfort in use. Those above shown auxiliary surfactants function as a thickening agent for the principal base. Since most of them are solid at a room temperature, however, separation easily occurs in storage. No storage stability is satisfactory.

SUMMARY OF THE INVENTION

A purpose of the invention is to provide a surfactant composition having an excellent foamability and thickening performance and then an excellent storage stability.

The invention provide a surfactant composition comprising the following components (a) and (b):
(a) at least one anionic surfactant selected from the group consisting of (1) to (3) defined below:
(1) a sulfonate-type anionic surfactant having an amide group or an ester group,
(2) a carboxylate-type anionic surfactant,
(3) a phosphate-type anionic surfactant, (b) a compound prepresented by the formula (I):

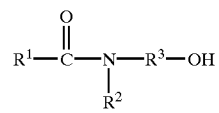

(I)

where $R^1CO-$ is a saturated or unsaturated acyl group having 6 to 24 carbon atoms which may have a hydroxy group, $R^2$ is an alkyl group having 1 to 3 carbon atoms and $R^3$ is a linear or branched chain alkylene group having 1 to 6 carbon atoms or a linear or branched chain alkenylene group having 2 to 6 carbon atoms.

The composition of the invention comprises (a) the anionic surfactant and (b) the N-alkanol-N-alkyl fatty acid amide in combination. (a) is limited to the specified species and (b) is provided with an excellent thicking property and an excellent foamability.

DETAILED DESCRIPTION OF THE INVENTION

The component (a) of the invention is an anionic surfactant selected from (1) to (3) shown above. One or a plurality of them maybe used. Among these anionic surfactants, (2) or (3) is preferred.

Examples of the sulfonate-type anionic surfactant (1) include an acylated amino sulfonic acid and a salt thereof, represented in the formula (II):

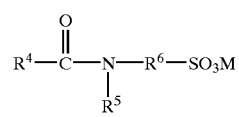

(II)

where $R^4CO-$ is a saturated or unsaturated acyl group having 6 to 24 carbon atoms, $R^5$ is a hydrogen atom or a linear or branched chain alkyl group having 1 to 3 carbon atoms which may possess —OH, —CN or —COOH as a substituent, preferably being a hydrogen atom or methyl group, $R^6$ is a linear or branched chain alkylene group having 1 to 4 carbon atoms or a linear or branched chain alkenylene group having 2 to 4 carbon atoms and M is a hydrogen atom, an alkali metal, an alkaline earth metal, ammonium or an alkanol amine;

an acylated hydroxyl sulfonic acid and a salt thereof, represented by the formula (III):

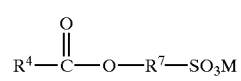

(III)

where $R^4CO-$ and M are the same as defined above and $R^7$ is a linear or branched chain alkylene group having 1 to 4 carbon atoms or a linear or branched chain alkenylene group of 2 to 4 carbon atoms;

a sulfonated compound of a lower alkyl ester of a fatty acid having 6 to 24 carbon atoms and a salt thereof, the alkyl preferably having 1 to 3 carbon atoms; and a sulfonated compound of a mono- or di-alkyl ester of a dicarboxylic acid of 3 to 9 carbon atoms and a salt thereof, the alkyl group preferably having 1 to 24 carbon atoms, more preferably 1 to 12.

More specifically is used at lease one of an acylated isethionate, an N-acyltaurate, an N-acyl-N-methyltaurate, a mono- or di-ester of sulfosuccinic salt and an α-sulfonated fatty acid ester salt.

All these sulfonate-type anionic surfactants have an acyl group having an amide group or an ester group. The acyl group is preferably a saturated or unsaturated group having 6 to 24 carbon atoms, more preferably 8 to 18 carbon atoms. Specific examples are acyl groups derived from octanoic acid, decanoic acid, dodecanoic acid, tetradecanoic acid, hexadecanoicacid, octadecanoic acid, docosanoic acid, linolic acid, 2-ethyl hexanoic acid, 2-octyl undecanoic acid, isostearic acid, oleic acid, coconut oil fatty acid, palm oil fatty acid, palm kernel oil fatty acid, tallow fatty acid, etc. Among these acyl groups, those containing 50 wt. % or more of an acyl group derived from a fatty acid having 12 to 14 carbon atoms are further preferable.

Examples of the carboxylate-type surfactant (2) include soap, an alkylethoxycarboxylate, an acylated amino acid salt, etc. As the soap, a fatty acid salt having 6 to 24 carbon atoms is preferred. Specific examples are octanoate, decanoate, dodecanoate, tetradecanoate, hexadecanoate, octadecanoate, docosanoate, linoleate, 2-ethylhexanoate, 2-octylundecanoate, isostearate, oleate, coconut oil fatty acid salt, palm oil fatty acid salt, palm kernel oil fatty acid salt, tallow fatty acid salt and a mixture thereof.

A preferred alkylethoxycarboxylate is expressed by the formula (IV):

$$R^8O(CH_2CH_2O)_nCH_2COOM \quad (IV)$$

where $R^8$ is a linear or branched chain alkyl or alkenyl group having 6 to 24 carbon atoms, n is a number of from 0 to 20 and M is the same as defined above.

A preferred acylated amino acid salt includes an acyl sarcosinate, an acyl glutamate, an acyl alanate and an acyl glycinate, having 6 to 24 carbon atoms in the acyl group, preferably 8 to 18.

Examples of the phosphate-type anionic surfactant (3) are phosphates expressed by the formulae (V) and (VI):

(V)

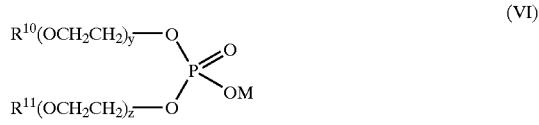

(VI)

where $R^9$, $R^{10}$, and $R^{11}$ are a linear or branched chain alkyl or alkenyl group of 8 to 18 carbon atoms, M is the same as defined above and plural M's may be either the same as or different from one another and x, y, and z are a number of from 0 to 10.

One or more of them may be used. A preferred phosphate has a linear or branched chain alkyl of 8 to 14 carbon atoms and the average addition mole number of ethylene oxide, expressed by x, y, z, of 0 to 6. The compound expressed by the formula (V) is particularly preferred.

A counter ion, expressed by M in formulas (II) to (VI), to form the anionic surfactants of (1) to (3) is selected from a hydrogen atom, an alkali metal, an alkaline earth metal, ammonium and an alkanol amine having a hydroxyl alkyl group of 2 to 3 carbon atoms. A preferred example thereof is hydrogen atom, sodium, potassium, magnesium, calcium, ammonium or mono-, di- or tri-ethanol amine, more preferably being hydrogen atom, sodium, potassium or ammonium.

In the component (b) of the present invention, $R^1CO$— is an acyl group as mentioned above. It is preferably a saturated or unsaturated acyl group having 8 to 18 carbon atoms. It includes for example an acyl group derived from octanoic acid, decanoic acid, dodecanoic acid, tetradecanoic acid, hexadecanoic acid, octadecanoic acid, docosanoic acid, linoleic acid, 2-ethylhexanoic acid, 2-octylundecanoic acid, isostearic acid, oleic acid, coco-fatty acid, a palm oil-fatty acid, a palm kernel oil-fatty acid or a tallow-fatty acid.

It is preferable among the acyl groups to include 50 wt. % or more of an acyl group derived from a fatty acid having 12 to 14 carbon atoms. It is more preferable to include 40 to less than 100 wt. % of an acyl group derived from a fatty acid having 12 carbon atoms.

In order not to lower foamability, $R^2$ is a linear or branched alkyl group having 1 to 3 carbon atoms, preferably methyl group or ethyl group. Methyl group is in particular preferable. In order not to lower the surface-active performance, $R^3$ is a linear or branched alkylene having 1 to 6 carbon atoms or an alkenylene group having 2 to 6 carbon atoms. It is preferably a linear or branched alkylene group having 2 or 3 carbon atoms.

The component (b) includes, for instance, N-(2-hydroxyethyl)-N-methyl octanamide, N-(2-hydroxyethyl)-N-methyl decanamide, N-(2-hydroxyethyl)-N-methyl dodecanamide, N-(2-hydroxyethyl)-N-methyl tertadecanamide, N-(2-hydroxyethyl)-N-methyl hexadecanamide, N-(2-hydroxyethyl)-N-methyl octadecanamide, N-(2-hydroxyethyl)-N-methyl-coco-fatty carboxamide, N-(2-hydroxyethyl)-N-methyl-palm kernel oil-fatty carboxamide, N-(2-hydroxypropyl)-N-ethyl dodecanamide, N-ethyl-N-(2-hydroxypropyl) oleamide and N-ethyl-N-(2-hydroxypropyl) isostearamide.

A method for producing the component (b) is not particularly limited. For example, it can be produced by a condensation reaction or a de-alcohol reaction of a fatty acid or a lower alcohol ester of a fatty acid with an alkanolamine, a reaction of a fatty acid halide with an alkanolamine in the presence of an alkaline catalyst, an ester-amide exchanging reaction (an aminolysis) between fats and oils and an alkanolamine or others. The product obtained by such a method may often contain small amounts of fatty acids, inorganic salts, glycerol and the like.

The blending rate of the component (a) to the component (b) in the composition of the invention is preferred to be a ratio by weight of (a)/(b)=99/1 to 50/50 from the viewpoint of foamability and thickening, more preferably 98/2 to 90/10.

The sum total of the components (a) and (b) in the composition of the invention is preferred to be 5 to 100 wt. % from the viewpoint of an excellent surface activity, more preferably 10 to 100 wt. %.

In addition to the essential components (a) and (b), in the invention, at least one selected from group consisting of a compound expressed by the formula (VII) (hereinafter called compound VII) and a compound expressed by the formula (VIII) (hereinafter called compound VIII) may be blended:

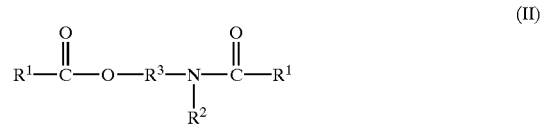

(II)

-continued $$R^1-\overset{O}{\underset{\|}{C}}-O-R^3-\underset{H}{N}-R^2 \quad (III)$$

$$R^1-\overset{O}{\underset{\|}{C}}-O-R^3-\underset{\underset{R^2}{|}}{N}-\overset{O}{\underset{\|}{C}}-R^1 \quad (VII)$$

$$R^1-\overset{O}{\underset{\|}{C}}-O-R^3-NH-R^2 \quad (VIII)$$

in the formula, R¹CO—, R² and R³ of the formulae have the same meanings as above shown and, in each compound, R¹, R² and R³ may be the same as or different from one another.

The compound represented by the formula (VII) includes, for instance, N-octanoyl-N-methylaminoethyl octanoate, N-octanoyl-N-methylaminoethyl decanoate, N-octanoyl-N-methylaminoethyl dodecanoate, N-octanoyl-N-methylaminoethyl tetraecanoate, N-octanoyl-N-methylaminoethyl hexadecanoate, N-octanoyl-N-methyaminoethyl octadecanoate, N-dodecanoyl-N-methylaminoethyl octanoate, N-dodecanoyl-N-methylaminoethyl decanoate, N-dodecanoyl-N-methylaminoethyl dodecanoate, N-dodecanoyl-N-methylaminoethyl tetradecanoate, N-dodecanoyl-N-methylaminoethyl hexadecanoate, N-dodecanoyl-N-methylaminoethyl octadecanoate, N-dodecanoyl-N-ethylaminohexyl octanoate, N-dodecanoyl-N-ethylaminohexyl decanoate, N-dodecanoyl-N-ethylaminohexyl dodecanoate, N-dodecanoyl-N-ethylaminohexyl tetradecanoate, N-dodecanoyl-N-ethylaminohexyl hexadecanoate, N-dodecanoyl-N-ethylaminohexyl octadecanoate, coco-fatty acid (N-cocoyl-N-methylaminoethyl)ester and palm kernel oil fatty acid (N-palm kerneloyl-N-methylaminoethyl ester.

Examples of the compound represented by the formula (VIII), for instance, include 2-(methylamino)ethyl octanoate, 2-(methylamino)ethyl decanoate, 2-(methylamino)-ethyl dodecanoate, 2-(methylamino)ethyl tetradecanoate, 2-(methylamino)ethyl hexadecanoate, 2-(methylamino)ethyl octadecanoate, 2-(methylamino)ethyl oleate, 2-(ethylamino)ethyl octanoate, 2-(ethylamino)ethyl dodecanoate, 2-(ethylamino)ethyl tetradecanoate, 2-(ethylamino)ethyl hexadecanoate, 2-(ethylamino)ethyl octadecanoate, 2-(ethylamino)ethyl oleate, 2-(methylamino) propyl octanoate, 2-(methylamino)propyl decanoate, 2-(methylamino)propyl dodecanoate, 2-(methylamino) propyl tetradecanoate, 2-(methylamino)propyl hexadecanoate, 2-(methylamino)propyl octadecanoate, 2-(methylamino)propyl oleate, a coco-fatty acid(2-ethylaminoethyl) ester and palm kernel fatty acid (2-ethylaminoethyl) ester.

The total blending amount of the compounds VII and VIII to the component (b) is preferably a rate by weight of (b)/(VII and VIII) of 99.99/0.01 to 80/20.

In addition to the above shown components, in the invention, an anionic surfactant other than the component (a), a cationic surfactant, a non-ionic surfactant, an amphoteric surfactant or a mixture thereof may be added as another component.

The surfactant composition of the invention can exhibit the characteristics sufficiently, regardless of its pH value. In particular, a preferred foamability and thickening property can be obtained in the pH range of 3.0 to 11.0.

EXAMPLES

Examples 1 to 7, Comparative Examples 1 to 7

Using the following components, various surfactant compositions shown in Table 1 were prepared and then evaluatead in view of foamability and storage stability by the following methods. Results are shown in Table 1. The viscosity was also determined by the following method. Results are shown in Table 2.

Components

Component (a)
a-1: sodium α-sulfonated lauric acid methylester
a-2: Sodium lauryl ethoxy (3) acetate
a-3: Sodium laurate
a-4: potassium monolauryl phosphate
a-5: potassium monolauryl ethoxy (3) phosphate
Component (b)
b-1: N-ethanol-N-methyl dodecanamide
b-2: N-ethanol-N-methyl palm kernel oil fatty acid amide
Other Component
c-1: Coconut oil fatty acid diethanolamide
c-2: Coconut oil fatty acid monoethanolamide Formability 30 mL of an aqueous solution of the surfactant composition was prepared by diluting it in deionized water to 20-fold. The aqueous solution was placed in a 300-mL mess cylinder having the inner diameter of 3 cm, equipped with a stop cock and shaken at 25° C. for 10 seconds with an amplitude having 10 cm 20 times. The volume (mL) of foam was immediately determined.

Storage Stability

The surfactant composition was allowed to stand at 0° C. for 1 week and then the appearance was observed visually.

○: Uniformly clear with no change

Δ: Turbid x: Separation, sedimentation or crystals' precipitation

Viscosity

The viscosity of the surfactant composition was measured at 25° C. with a standard B type viscometer.

TABLE 1

| | Example | | | | | | | Comparative example | | | | | | |
|---|---|---|---|---|---|---|---|---|---|---|---|---|---|---|
| | 1 | 2 | 3 | 4 | 5 | 6 | 7 | 1 | 2 | 3 | 4 | 5 | 6 | 7 |

Composition of
surface active agents
(parts by weight)

TABLE 1-continued

| | | Example | | | | | | | Comparative example | | | | | | |
|---|---|---|---|---|---|---|---|---|---|---|---|---|---|---|---|
| | | 1 | 2 | 3 | 4 | 5 | 6 | 7 | 1 | 2 | 3 | 4 | 5 | 6 | 7 |
| Component (a) | a-1 | 18 | | | | | | | 20 | | | | | | |
| | a-2 | | 20 | | | | | | | 20 | | | | | |
| | a-3 | | | 16 | | | | | | | 20 | | | | |
| | a-4 | | | | 13 | 16 | | | | | | 20 | | 16 | |
| | a-5 | | | | | | 14 | 14 | | | | | 20 | | 15 |
| Component (b) | b-1 | 2 | 5 | | 7 | | 6 | | | | | | | | |
| | b-2 | | | 4 | | 4 | | 6 | | | | | | | |
| Other component | c-1 | | | | | | | | | | | | | | 5 |
| | c-2 | | | | | | | | | | | | | 4 | |
| Result of evaluation | | | | | | | | | | | | | | | |
| Bubble amount (mL) | | 150 | 150 | 171 | 242 | 246 | 240 | 255 | 67.6 | 70 | 105 | 200 | 61 | 205 | 213 |
| Storage stability | | ○ | ○ | ○ | ○ | ○ | ○ | ○ | Δ | Δ | Δ | ○ | ○ | X | X |

TABLE 2

| | | Example | | | | | | Comparative example | | | | | |
|---|---|---|---|---|---|---|---|---|---|---|---|---|---|
| | | 1 | 2 | 4 | 5 | 6 | 7 | 1 | 2 | 4 | 5 | 6 | 7 |
| Composition of surface active agents | | | | | | | | | | | | | |
| Component (a) | a-1 | 18 | | | | | | 20 | | | | | |
| | a-2 | | 20 | | | | | | 20 | | | | |
| | a-4 | | | 13 | 16 | | | | | 20 | | 16 | |
| | a-5 | | | | | 14 | 14 | | | | 20 | | 15 |
| Component (b) | b-1 | 2 | 5 | 7 | | 6 | | | | | | | |
| | b-2 | | | | 4 | | 6 | | | | | | |
| Other component | c-1 | | | | | | | | | | | | 5 |
| | c-2 | | | | | | | | | | | 4 | |
| Viscosity (mPa · s) | | 48 | 130 | 3400 | 3250 | 3870 | 2011 | 12.1 | 15.5 | 1023 | 14.8 | 5350 | 830 |

What is claimed is:

1. A surfactant composition consisting essentially of the following components (a) and (b):

(a) at least one phosphate anionic surfactant,
   (b) a compound represented by formula (I):

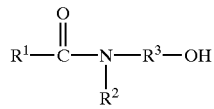

(I)

where $R^1CO-$ is a saturated or unsaturated acyl group having 6 to 24 carbon atoms which may have hydroxy group, $R^2$ is an alkyl group having 1 to 3 carbon atoms and $R^3$ is a linear or branched chain alkylene group having 1 to 6 carbon atoms or a linear or branched chain alkenylene group having 2 to 6 carbon atoms.

2. The composition of claim 1, wherein the ratio by weight of the component (a) to the component (b) is in a range of (a)/(b)=99/1 to 50/50.

3. The composition of claim 1, wherein the at least one phosphate anionic surfactant is represented by formula (V) or (VI):

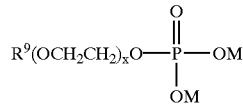

(V)

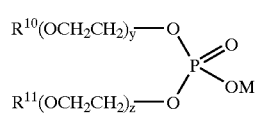

(VI)

where $R^9$, $R^{10}$, and $R^{11}$ are an alkyl or alkenyl group of 8 to 18 carbon atoms, M is hydrogen atom, an alkali metal, an alkaline earth metal, ammonium or an alkanol amine, wherein M may be the same as or different from one another, and x, y, and z are a number ranging from 0 to 10.

4. The composition of claim 3, wherein M is an alkali metal.

5. The composition of claim 3, wherein the acyl group has from 8 to 18 carbon atoms.

6. The composition of claim 5, wherein the acyl group is derived from at least one of octanoic acid, decanoic acid, dodecanoic acid, tetradecanoic acid, hexadecanoic acid, octadecanoic acid, docosanoic acid, linolic acid, 2-ethyl hexanoic acid, 2-octyl undecanoic acid, isostearic acid, oleic acid, coconut oil fatty acid, palm oil fatty acid, palm kernel oil fatty acid, or tallow fatty acid.

7. The composition of claim 1, wherein the ratio by weight of (a)/(b) is from 98/2 to 90/10.

8. The composition of claim 1, wherein at least one of potassium monolauryl phosphate or potassium monolauryl ethoxy (3) phosphate, is present.

9. The composition of claim 1, wherein the at least one phosphate anionic surfactant is represented by formula (V):

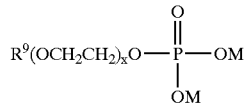
(V)

wherein $R^9$ is an alkyl or alkenyl group of 8 to 18 carbon atoms, M is hydrogen atom, an alkali metal, an alkaline earth metal, ammonium or an alkanol amine, wherein M may be the same as or different from one another, and x is a number ranging from 3 to 10.

10. A surfactant composition comprising
   (a) at least one anionic surfactant selected from the group consisting of:
      an acylated amino sulfonic acid or salt thereof of formula (II)

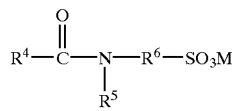
(II)

where $R^4CO$— is a saturated or unsaturated acyl group having 6 to 24 carbon atoms, $R^5$ is a hydrogen atom or a linear or branched chain alkyl group having 1 to 3 carbon atoms which may possess —OH, —CN or —COOH as a substituent, $R^6$ is a linear or branched chain alkylene group having 1 to 4 carbon atoms or a linear or branched chain alkenylene group having 2 to 4 carbon atoms and M is hydrogen atom, an alkali metal, an alkaline earth metal, ammonium or an alkanol amine;
      an acylated sulfonic acid or a salt thereof, of formula (III):

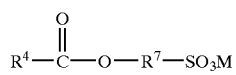
(III)

where $R^4CO$— and M are the same as defined above and $R^7$ is a linear or branched chain alkylene group having 1 to 4 carbon atoms or a linear or branched chain alkenylene group of 2 to 4 carbon atoms; and a phosphate anionic surfactant of formula (V):

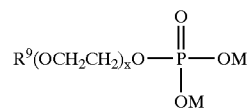
(V)

wherein $R^9$ is an alkyl or alkenyl group of 8 to 18 carbon atoms, M is hydrogen atom, an alkali metal, an alkaline earth metal, ammonium or an alkanol amine, wherein M may be the same as or different from one another, and x is a number ranging from 3 to 10; and (b) at least one compound of formula (I):

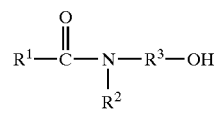
(I)

where $R^1CO$— is a saturated or unsaturated acyl group having 6 to 24 carbon atoms which may have hydroxy group, $R^2$ is an alkyl group having 1 to 3 carbon atoms and $R^3$ is a linear or branched chain alkylene group having 1 to 6 carbon atoms or a linear or branched chain alkenylene group having 2 to 6 carbon atoms, wherein at least one phosphate anionic surfactant of formula (V) is present.

11. The composition of claim 10, wherein the ratio by weight of the anionic surfactant to the compound of formula (I)((a)/(b)) is from 99/1 to 50/50.

12. The composition of claim 10, comprising at least one sulfonic acid-containing anionic surfactant.

13. The composition of claim 10, wherein M is an alkali metal.

14. The composition of claim 10, wherein a compound of formula (II) is present and $R^5$ is a hydrogen atom or a methyl group.

15. The composition of claim 10, comprising at least one of an acylated isethionate, an N-acyltaurate or an N-acyl-N-methyltaurate.

* * * * *

UNITED STATES PATENT AND TRADEMARK OFFICE
CERTIFICATE OF CORRECTION

PATENT NO. : 6,946,430 B2
DATED : September 20, 2005
INVENTOR(S) : Sakai et al.

It is certified that error appears in the above-identified patent and that said Letters Patent is hereby corrected as shown below:

Title page,
Items [45] and [*] Notice, should read as follows:

-- [45]  Date of Patent:    *Sep. 20, 2005 --.

-- [*]  Notice:   Subject to any disclaimer, the term of this patent is extended or adjusted under 35 U.S.C. 154(b) by 117 days.

This Patent is subject to a terminal disclaimer. --.

Signed and Sealed this

Twenty-second Day of November, 2005

JON W. DUDAS
*Director of the United States Patent and Trademark Office*